US007333190B1

(12) United States Patent
Pendell-Jones et al.

(10) Patent No.: US 7,333,190 B1

(45) Date of Patent: Feb. 19, 2008

(54) RAMAN INTERROGATION OF THREAT AEROSOLS

(75) Inventors: James E. Pendell-Jones, Baltimore, MD (US); Patrick Ponsardin, Placita, NM (US); Robert Almassy, Alexandria, VA (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 0 days.

(21) Appl. No.: 11/586,497

(22) Filed: Oct. 26, 2006

(51) Int. Cl.
*G01N 21/65* (2006.01)
*G01J 3/44* (2006.01)

(52) U.S. Cl. ........................ 356/73; 356/301; 356/318; 250/461.1

(58) Field of Classification Search ................ 356/301, 356/318, 73; 250/461.1
See application file for complete search history.

(56) References Cited

U.S. PATENT DOCUMENTS 4,689,052 A 8/1987 Ogren et al.
7,113,275 B2 * 9/2006 Gardner et al. ............. 356/301
2006/0061762 A1 * 3/2006 Dwight et al. .............. 356/301

OTHER PUBLICATIONS

S. Hong, J. Birmingham, M. Fountain, "Mesochannel Gas Sampler for Rapid Sample Collection and Concentration," Mar. 2001, pp. 1-15, Prepared for the Department of Energy Under DOE Grant No. DE-FG03-00ER83048 by MesoSystems Technology, Inc. Kennewich, Washington.

Lockheed Martin Maritime Systems & Sensors, "Biological Aerosol Warning System," Cleared for Public Domain Release DoD/00-S-0607, Dec. 1999, Aug. 2003, Manassas, VA.

General Dynamics Armament and Technical Products, "Biological Agent Warning Sensor," 2007, Charlotte, NC.

* cited by examiner

*Primary Examiner*—F. L. Evans
*Assistant Examiner*—Abdullahi Nur
(74) *Attorney, Agent, or Firm*—Edell, Shapiro & Finnan, LLC

(57) ABSTRACT

A system and method are provided for detecting non-fluorescing aerosol particles of biological origin within ambient background aerosol particles using Raman spectroscopy.

26 Claims, 4 Drawing Sheets

```
┌─────────────────────────────────────────────────────┐
│ COLLECTING/SAMPLING A VOLUME OF AIR IN WHICH AEROSOLS│──110
│              MAY BE SUSPENDED                        │
└─────────────────────────────────────────────────────┘
                          ↓
        ┌──────────────────────────────────────┐
        │ SEPARATING AEROSOL PARTICLES FROM THE│──120
        │         COLLECTED/SAMPLED AIR        │
        └──────────────────────────────────────┘
                          ↓
        ┌──────────────────────────────────────┐
        │ CONCENTRATING/IMPACTING THE AEROSOL  │──130
        │        PARTICLES ONTO A SURFACE      │
        └──────────────────────────────────────┘
                          ↓
    ┌──────────────────────────────────────────────┐
    │ DIRECTING A BEAM OF ULTRAVIOLET LIGHT TO THE │──140
    │     PARTICLES TO EXCITE RAMAN SCATTERING     │
    └──────────────────────────────────────────────┘
                          ↓
    ┌──────────────────────────────────────────────┐
    │ CAPTURING THE SCATTERED OPTICAL ENERGY       │──150
    │     (INCLUDING RAMAN SCATTERED ENERGY)       │
    └──────────────────────────────────────────────┘
                          ↓
    ┌──────────────────────────────────────────────┐
    │ DISPERSING THE RAMAN SCATTERED ENERGY ONTO A │──160
    │    DETECTOR TO PRODUCE A RAMAN SPECTRA       │
    └──────────────────────────────────────────────┘
                          ↓
    ┌──────────────────────────────────────────────┐
    │ ANALYZING THE RAMAN SPECTRA TO DETECT A NON- │──170
    │ FLUORESCING BIOLOGICAL SUBSTANCE IN THE PARTICLES│
    └──────────────────────────────────────────────┘
```

100

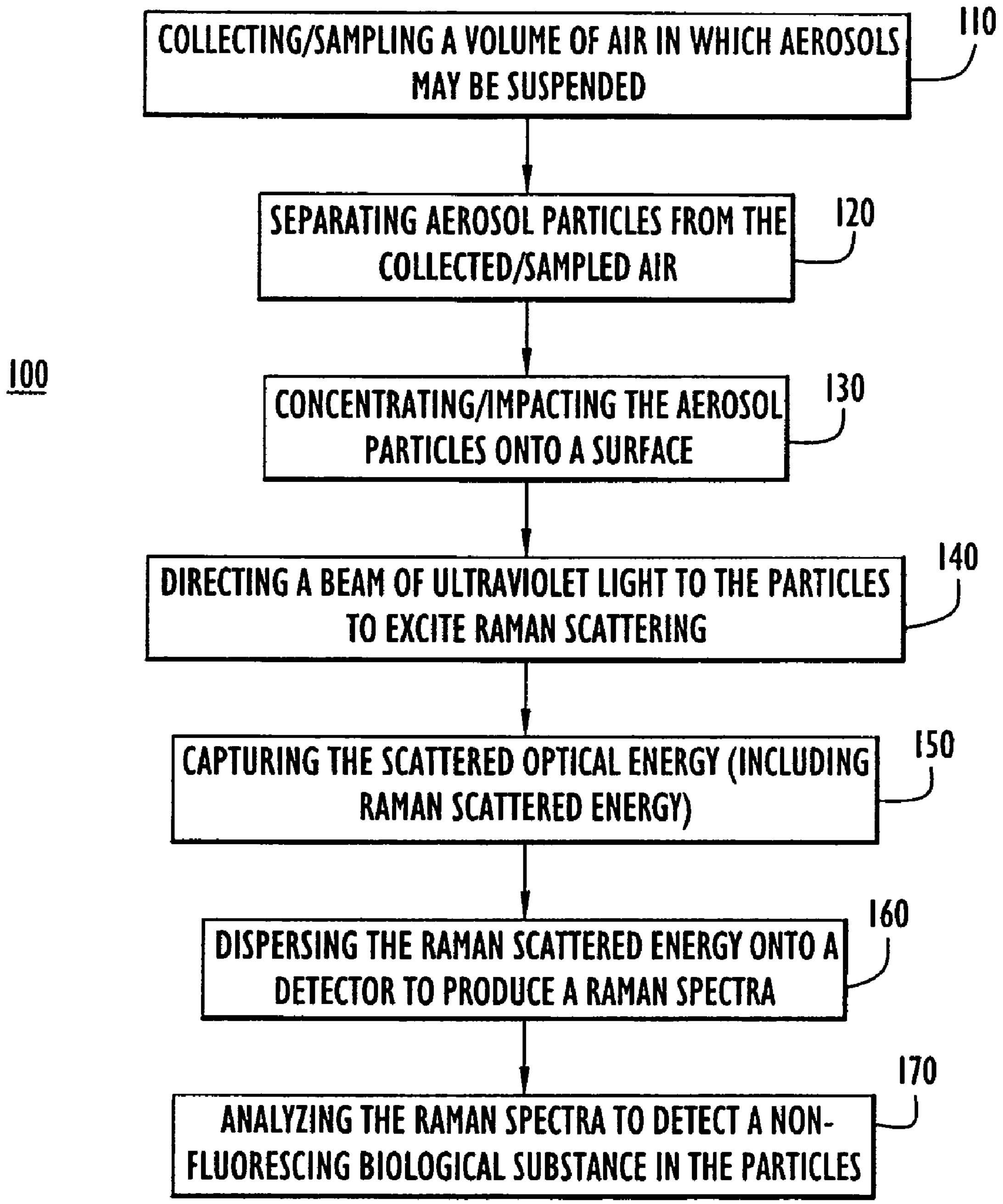

FIG.3

RAMAN INTERROGATION OF THREAT AEROSOLS

BACKGROUND OF THE INVENTION

In the field of monitoring for substances harmful to humans that may be inadvertently or intentionally deployed, there is a need to be able to detect biological substances that do not fluoresce when excited by light, and in particular airborne aerosol particles that may contain such harmful biological substances. The detection of non-fluorescing biological substances represents an important gap in the capabilities of detection systems and techniques heretofore known.

SUMMARY OF THE INVENTION

Briefly, a system and method are provided for detecting non-fluorescing aerosol particles of biological origin within ambient background aerosol particles using Raman spectroscopy.

BRIEF DESCRIPTION OF THE DRAWINGS

FIG. 3 is a flow diagram depicting operation of the system according to an embodiment of the invention.

DETAILED DESCRIPTION

Figure 1:
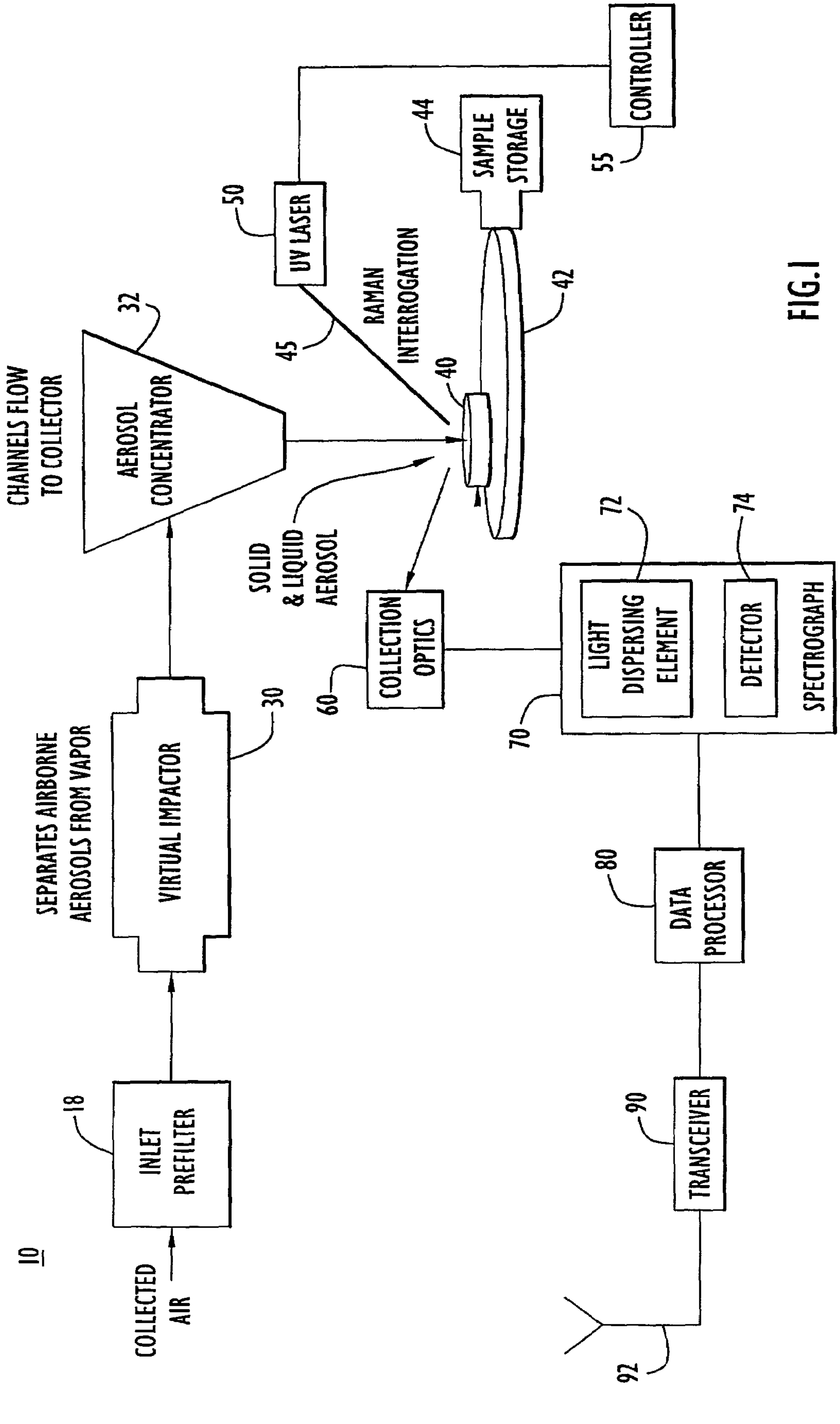
FIG. 1 is a block diagram of a detection system according to an embodiment of the present invention.
Figure 2:
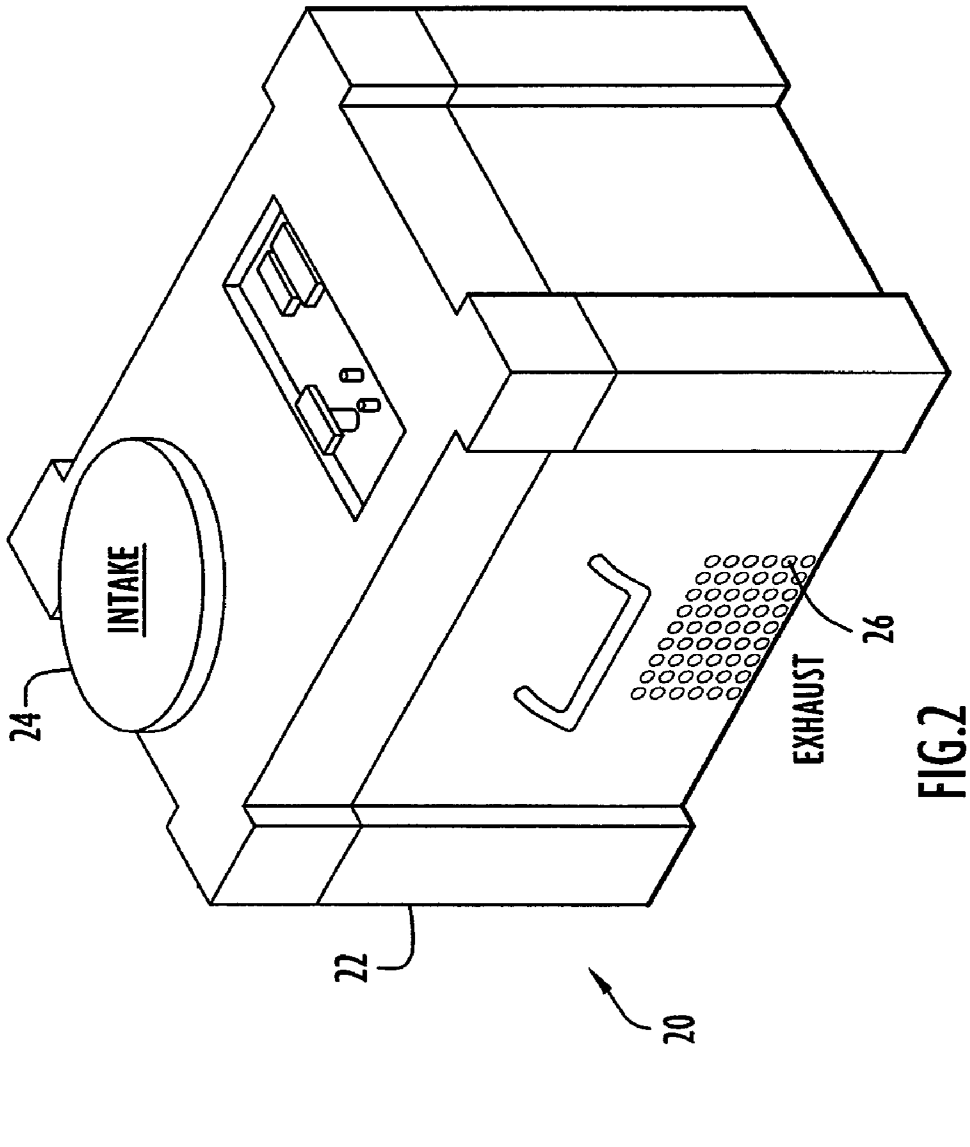
FIG. 2 is a perspective view of an air sampler device useful to house the detection system shown in FIG. 1 according to an embodiment of the invention.

Referring first to FIGS. 1 and 2, the detection system according to an embodiment of the invention is generally shown at 10. The detection system 10 comprises a plurality of components that may be contained within an air sampler 20. As shown in FIG. 2 according to one embodiment, the air sampler 20 comprises a body or housing 22 having an intake port 24 and an exhaust port 26. The intake port 24 draws in air and any airborne (aerosol) particles in the air. To this end, one or more pumps and a motor driven blower fan (not shown) may be provided in the housing 22 to draw air through the intake port and pass exhaust to the exhaust port.

The system 10 comprises an inlet prefilter 18 through which collected air passes. The output of the inlet prefilter is coupled to a virtual impactor 30. The inlet prefilter 18 is a mechanical device that acts like a self cleaning filter to prevent larger particles from entering the housing 22 and interfering with operation of the virtual impactor 30. The remaining components of the system 10 comprise an aerosol concentrator 32, a sample collector 40, a carousel 42, a sample storage container 44, an ultraviolet (UV) laser light source 50, collection optics 60, a spectrograph 70, a data processor 80 and optionally a transceiver 90. A controller 55 is connected to the UV laser light source 50 to control when and for how long the light source 50 is activated. The UV laser light source 50 may be capable of producing deep UV light that is light in a wavelength region less than 263 nm. The controller 500 may also be coupled to other devices that include electronic components. In the system shown in FIG. 1, it should be understood that the functions of the data processor 80 and the controller 55 may be integrated into a single computing or data processing device.

The virtual impactor 30 is a device that sorts the aerosol particles out of the sampled air and directs those particles to the aerosol concentrator 32. Not by way of limitation, the virtual impactor 30 may be a MicroVIC® Particle Concentrator, manufactured by MesoSystems Technology, Inc. The aerosol concentrator 32 directs the aerosol particles (solid or liquid) through an impaction nozzle and to the sample collector 40. For example, the Micro VIC® is equipped with impaction nozzles that perform the function of the aerosol concentrator 32. Thus, in one embodiment, a single device may perform the functions of the virtual impactor 30 and the aerosol concentrator 32.

The sample collector 40 comprises a surface or collection media on which particles separated from the collected air are directed by the aerosol concentrator 32. The aerosol collection surface 40 is, for example, a disk or a plate shaped device. The aerosol cloud is accelerated through the aerosol concentrator 32 and directed at the sample collector 40. The aerosol particles, due to their inertia, impact directly on the sample collector 40.

The sample collector 40 continues to collect the particles until there is an amount sufficient for interrogation. In one embodiment, the sample collector 40 is a portion of a surface of the carousel 42. The carousel 42 rotates the collected particles to position to be illuminated by the UV laser light source 50 while aerosol particles are collected on a different portion of the carousel 42. For example, the carousel 42 may comprise a disk-shaped surface onto which particles separated from collected air are impacted or concentrated at one position of the disk, while particles previously collected and concentrated onto another position of the disk are illuminated by the UV laser light source 50. The disk is rotated for each new collection cycle. The UV laser light source 50, under control of the controller 55, illuminates the collected particles positioned by the carousel 42. After collected particles are interrogated, they may be offloaded from the carousel and stored in the sample storage container 44 for further analysis at a later point in time. This allows a user to perform additional confirmatory and forensic test on aerosol samples or threats.

The collection optics 60 collects the scattered energy (light) from the illuminated particles on the sample collector 40. For example, the collection optics 60 may comprise a telescope. The collection optics 60 also separates Raman scattering from Raleigh scattered energy, and passes the Raman scattering (scattered energy) to the spectrograph 70.

The spectrograph 70 comprises a light dispersing element 72 and a detector 74. The light dispersing element 72 may be a diffraction grating or prism and the detector 74 may be an intensified charge coupled device (ICCD), for example. The light dispersing element 72 uses dispersive optics to separate the constituent wavelengths (colors) of the light directed to it and directs the dispersed light onto the detector 74. The detector 74 detects the light intensity at each of a plurality of wavelength “bins” and produces a signal or digital data that representative thereof. The data processor 80 may be a computer, digital signal processor, programmable microcontroller or other computing device that analyzes the spectrum data produced by the spectrograph 70. The data processor 80 uses a stored library of known spectra and attempts to match the measured spectra (produced by the spectrograph 70) with the library spectra so as to identify a substance in the collected and sampled particles. The results of the analysis may then be supplied to the transceiver 90 for transmission to a remote device for further study or for informational purposes. The transceiver 90 may receive commands from a remote controller or device and in response transmit reports concerning the substances that the system 10 has detected. The transceiver 90 may employ wired communication techniques or wireless (e.g., radio frequency) communication techniques via antenna 92.

Reference is now made to FIG. 3 (with continued reference to FIGS. 1 and 2) for a description of the operation of the detection system 10 and a detection method 100 according to an embodiment of the invention. At 110, air in which aerosols may be suspended is drawn through into the air sampler 20 and through the virtual impactor 30. At 120, the virtual impactor 30 separates aerosol particles from the collected air producing a major flow and a minor flow. The aerosol particles are contained in the minor flow produced by the virtual impactor 30 and at 130 are directed to the sample collector 40 via the aerosol concentrator 32. Next, at 140, the UV light source 50 is activated to direct a beam of UV light to the particles on the sample collector 40 in order to excite Raman scattering. At 150, the scattered optical energy is captured by the collection optics 60 and the Raman scattering is separated from the Raleigh scattering. At 160, the Raman scattering is directed to the spectrograph 70 where it is dispersed into its constituent wavelengths by the light dispersing element 72 and directed onto the detector 74 to produce a Raman data. At 170, the Raman data is analyzed in order to detect non-fluorescing biological substances in the collected aerosol particles.

As indicated above, the method 100 is continuous. While new volumes of air are collected (110), aerosol particles separated (120) from the air are impacted (130) on one portion of the surface of the carousel 42, UV light is directed (140) onto another portion of the carousel 42 to illuminate particles collected thereby exciting Raman scattering, capturing (150) the scattered optical energy from the particles and directing the scattered optical energy to a detector of the spectrograph 70 for to enable analysis (170) of the Raman data produced by the detector of the spectrograph 70. In one embodiment, the air collection, particle separation and particle impacting/concentrating steps (110-130) are continuously performed with respect to newly collected air to impact an amount of particles onto the surface sufficient for analysis, and the interrogation and analysis steps (140, 150, 160 and 170) are performed generally without deviating from a time interval necessary for collecting the amount of particles necessary for interrogation on the surface of the collector. Moreover, the interrogation and analysis steps (140, 150, 160 and 170) may be performed with respect to all particles on the surface that are illuminated within a field of view without targeting a particular portion of the field of view.

Thus, according to an embodiment of the present invention, Raman (bond vibrational) spectra produced when a molecule is illuminated with light is analyzed to detect substances, in particular biological substances that do not fluoresce. By using Raman spectra to detect non-fluorescing biological substances, there is no need for complex targeting techniques involving changing optical focus depth and/or rejecting portions of an image space based on the absence of signal in a particular wavelength region. Said another way, because the detection system and method described herein uses very short wavelength excitation light, the Raman return signal will be very strong. Therefore, even for those substances that do not fluoresce, their Raman scattering is strong enough to detect them when comparing the Raman spectrum against a library.

Figure 4:
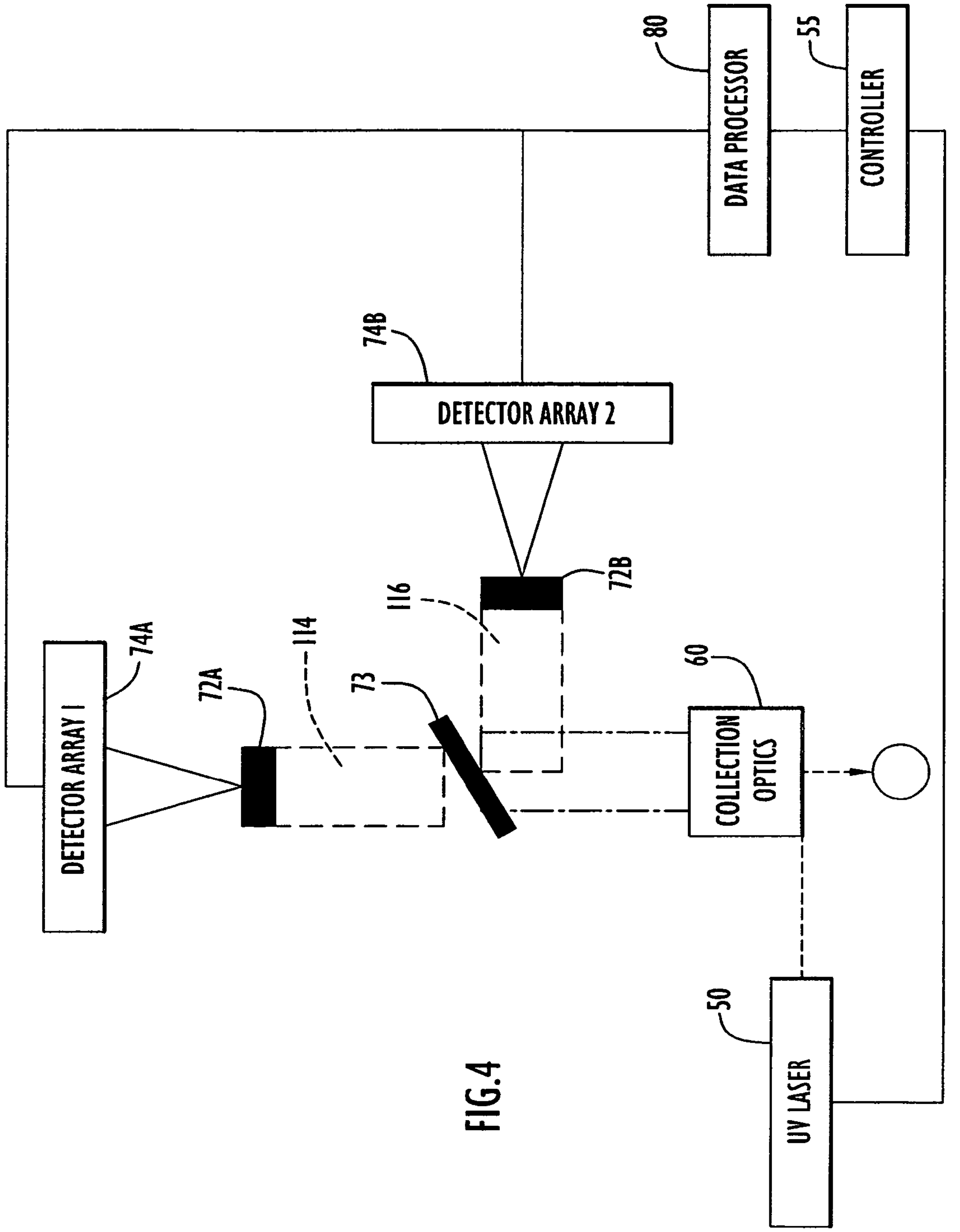
FIG. 4 is a block diagram illustrating additional capability that may be added to the detection system shown in FIG. 1 according to another embodiment of the present invention.

Turning to FIG. 4, another embodiment of the invention is described. In this embodiment, the detection system 10 is modified to simultaneously collect Raman scattering and fluorescence scattering in response to UV illumination of collected aerosol particles. The UV illumination is in the "deep" UV wavelength region (less than 263 nm) so that the Raman scattering and the fluorescence scattering are in different wavelength regions. To this end, there are two light dispersing elements 72A and 72B and a wavelength selective optical element 73. The wavelength selective optical element 73 separates the Raman scattering from fluorescence scattering since they are in two different wavelength regions. By way of example only, the wavelength selective optical element 73 is a dichroic mirror, tunable bandpass filter or reflective Kerr medium capable of directing Raman scattering 114 in a first wavelength region to the first light dispersing element 72A and directing fluorescence scattering 116 in a second wavelength region to a second light dispersing element 72B. For example, the Raman scattering is in a first wavelength region extending 263 nm to 284 nm and the fluorescence scattering is in a second wavelength region extending from 284 nm to 550 nm. The light dispersing element 72A separates out the constituent wavelengths of the Raman scattering and directs those wavelengths of light to a detector 74A. The light dispersing element 74A separates out the constituent wavelengths of fluorescence scattering and directs those wavelengths of light to a detector 74B.

The first detector 74A detects the light intensity at each of a plurality of wavelength bins and produces a signal or Raman digital data that represents the Raman scattering. The second detector 74B detects the light intensity at each of a plurality of wavelength bins and produces a signal or fluorescence digital data that represents the fluorescence scattering. By way of example, the first detector 74A may be a gated detector array such as an ICCD that converts the incoming spectra to digital data. Similarly, the second detector 74B is an ICCD, or an array of very fast gated photodiodes that can capture not only the shape of the fluorescence spectra but also the snapshots of the fluorescence spectra at multiple time instances over a time interval following a pulse or burst of the UV light beam 45 for purposes of deriving the fluorescence lifetime at one or more detection wavelengths. Thus, Raman spectra and fluorescence spectra are simultaneously captured from a single pulse or burst of UV light, or average such data obtained as a result of each of several pulses of UV light.

The data processor 80 can then analyze the Raman data and fluorescence data. Moreover, the data processor 80 may compute fluorescence lifetime data at one or more detection wavelengths from fluorescence data obtained from the second detector 74B at each of the plurality of time instances (hereinafter referred to as the "fluorescence samples") over the time interval following the UV light beam pulse or burst. Thus, the data processor may analyze the Raman spectra, fluorescence spectra and fluorescence lifetime at one or more wavelengths to characterize or identify substances.

Heretofore, it is not known to use Raman for detecting non-fluorescing substances. By using "deep" UV laser light, the Raman scattering will be in a different wavelength region than that of the background noise (e.g., fluorescence spectrum). As a result, the signal-to-interference ration (S/I) is relatively strong. These techniques can be used to continuously monitor particles extracted from collected air. The UV light employed by the techniques described herein will not degrade the particles.

Again, the spectroscopy techniques described herein do not require targeting. Targeting involves locating a particle of interest through highly complex algorithms that nearly always require human intervention or confirmation, and then subsequently "zooming" in on a particle of interest for more detailed analysis. Thus, targeting techniques do not allow for continuous monitoring, such as continuous monitoring of collected air. Furthermore, the techniques of the present invention do not rely on fluorescing or auto-fluorescing whereas prior art spectroscopy techniques for biological threats only use fluorescence analysis and therefore would not be able to detect non-fluorescing biological substances.

The system and methods described herein may be embodied in other specific forms without departing from the spirit or essential characteristics thereof. The foregoing embodiments are therefore to be considered in all respects illustrative and not meant to be limiting.

What is claimed is:

1. A method of using Raman spectroscopy for continuously monitoring air for detection of aerosols of biological origin that do not fluoresce, comprising:

a. capturing air to be analyzed;

b. separating aerosol particles that may be contained in the air;

c. impacting the aerosol particles onto a surface;

d. directing a beam of ultraviolet light to the particles on the surface in order to excite Raman scattering;

e. capturing the Raman scattering; and f. analyzing the Raman scattering to detect a non-fluorescing biological substance in said aerosol particles.

2. The method of claim 1, wherein during (d) directing, (e) capturing and (f) analyzing, said (a) capturing, (b) separating and (c) impacting are performed with respect to newly collected air to concentrate particles onto a portion of the surface while said (d) directing comprises directing the beam of ultraviolet light to particles on another portion of the surface.

3. The method of claim 2, wherein said (a) capturing, (b) separating and (c) impacting are continuously performed with respect to newly collected air to impact an amount of particles onto the surface sufficient for analysis, and wherein said (d) directing, (e) capturing and (f) analyzing are performed without deviation from a time interval necessary for collecting said amount of particles onto the surface.

4. The method of claim 1, wherein said (d) directing, (e) capturing and (f) analyzing are performed with respect to all particles within a field of view on the surface without targeting a particular portion of the field of view.

5. The method of claim 1, wherein said (c) collecting comprises collecting the aerosol particles on the surface that moves continuously or at time intervals so that the aerosol particles obtained from newly collected air are directed to an unoccupied portion of the surface.

6. The method of claim 5, and further comprising storing at least some of the aerosol particles that have been analyzed for further analysis at a later time.

7. The method of claim 1, wherein (d) directing comprises directing a beam of ultraviolet light in a wavelength region below 263 nm.

8. The method of claim 1, wherein (e) capturing comprises capturing scattered optical energy including the Raman scattering and fluorescence scattering, wherein the Raman scattering and the fluorescence scattering are in different wavelength regions, and further comprising separating the Raman scattering and the fluorescence scattering in the captured optical energy.

9. The method of claim 8, wherein (f) analyzing comprises analyzing the Raman scattering with a first detector to detect a non-fluorescing biological substance in said aerosol particles and analyzing the fluorescence scattering with a second detector to detect a fluorescing substance in the aerosol particles.

10. A method for detecting non-fluorescing aerosol particles of biological origin within ambient background aerosol particles using Raman spectroscopy, comprising:

a. directing a beam of ultraviolet light in a wavelength region below 263 nm to the aerosol particles in order to excite Raman scattering;

b. capturing scattered optical energy including the Raman scattering; and c. analyzing the Raman scattering to detect the non-fluorescing aerosol particles of biological origin.

11. The method of claim 10, wherein capturing comprises capturing scattered optical energy including the Raman scattering and fluorescence scattering resulting from substances other than non-fluorescing substances, wherein the Raman scattering and the fluorescence scattering are in different wavelength regions, and further comprising separating the Raman scattering and the fluorescence scattering in the captured optical energy.

12. The method of claim 11, wherein analyzing comprises analyzing the Raman scattering with a first detector to detect a non-fluorescing biological substance in said aerosol particles and analyzing the fluorescence scattering with a second detector to detect a fluorescing substance in the aerosol particles.

13. A spectroscopy system, comprising:

a. an air sampler comprising a housing having an intake port to collect air in which aerosols may be suspended;

b. a virtual impactor in said housing that separates aerosol particles that may be contained in the collected air;

c. a surface on which aerosol particles separated by the virtual impactor are directed;

d. an ultraviolet laser light source that directs a beam of ultraviolet light to the particles on the surface to excite Raman scattering;

e. at least one optical element that captures Raman scattering;

f. a spectrograph that receives the Raman scattering and produces Raman data representing intensity of constituent wavelengths of the Raman scattering; and g. a data processor coupled to the spectrograph that analyzes the Raman data to detect a non-fluorescing biological substance in the aerosol particles.

14. The system of claim 13, wherein the ultraviolet laser light source, at least one optical element and spectrograph reside within said housing.

15. The system of claim 13, wherein said virtual impactor continuously concentrates particles obtained from newly collected air onto a portion of the surface while the ultraviolet light source illuminates particles on another portion of the surface.

16. The system of claim 15, wherein the virtual impactor separates particles from newly collected air to impact an amount of particles onto the surface sufficient for analysis, and the ultraviolet light source and data processor are activated without deviation from a time interval necessary for collecting said amount of particles onto the surface.

17. The system of claim 16, wherein the ultraviolet light source is activated to direct a beam onto all particles within a field of view on the surface without targeting a particular portion of the field of view.

18. The system of claim 13, wherein the surface of the collector is moved continuously or at time intervals so that the aerosol particles obtained from newly collected air are directed an unoccupied portion of the surface.

19. The system of claim 18, and further comprising a storage container for storing at least some of the aerosol particles that have already been analyzed for further analysis at a later time.

20. The system of claim 13, wherein the ultraviolet laser light source produces a beam of ultraviolet light in a wavelength region below 263 nm.

21. The system of claim 13, wherein the ultraviolet laser light source excites scattered optical energy including the Raman scattering and fluorescence scattering resulting from substances contained in the particles, wherein the Raman scattering and the fluorescence scattering are in different wavelength regions, and further comprising a wavelength selective optical element that separates the Raman scattering and the fluorescence scattered energy in the scattered optical energy.

22. The system of claim 21, wherein the spectrograph comprises first and second light dispersing elements and first and second detectors, wherein the first light dispersing element disperses the Raman scattered energy into its constituent wavelengths and the first detector generates the Raman data from light directed to it by the first light dispersing element, and the second light dispersing element disperses the fluorescence scattered energy into its constituent wavelengths and the second detector generates fluorescence data from light directed to it by the second light dispersing element.

23. The system of claim 22, wherein the data processor analyzes the Raman data to detect a non-fluorescing biological substance and analyses the fluorescence data to detect a fluorescing substance.

24. The method of claim 8, wherein capturing comprises simultaneously capturing the Raman scattering and the fluorescence scattering excited as a result of a single pulse or burst of ultraviolet light.

25. The method of claim 11, wherein capturing comprises simultaneously capturing the Raman scattering and the fluorescence scattering excited as a result of a single pulse or burst of ultraviolet light.

26. The system of claim 22, wherein the first and second light dispersing elements simultaneously disperse the Raman scattering and fluorescence scattering, respectively, excited as a result of a single burst of ultraviolet light.

* * * * *